US00PP26416P3

(12) United States Plant Patent
Korlipara

(10) Patent No.: US PP26,416 P3
(45) Date of Patent: Feb. 16, 2016

(54) ***VERONICA* PLANT NAMED 'TNVERA'**

(50) Latin Name: ***Veronica* hybrid**
Varietal Denomination: TNVERA

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 119 days.

(21) Appl. No.: 14/120,291

(22) Filed: May 14, 2014

(65) Prior Publication Data

US 2015/0334892 P1 Nov. 19, 2015

(51) Int. Cl.
*A01H 5/00* (2006.01)

(52) U.S. Cl.
USPC ..... Plt./251

(58) Field of Classification Search
USPC ..... Plt./251
See application file for complete search history.

*Primary Examiner* — Susan McCormick Ewoldt
(74) *Attorney, Agent, or Firm* — Klarquist Sparkman, LLP

(57) ABSTRACT

A new and distinct form of *Veronica* plant characterized by warm pink flowers in free flowering spikes, with some rebloom in late summer, a compact, slow spreading, low mounding habit, excellent dense branching with flower spikes at end of every branch, medium green leaves, excellent vigor, and good garden performance.

1 Drawing Sheet

Botanical denomination: *Veronica* hybrid.
Variety designation: 'TNVERA'.

BACKGROUND OF THE INVENTION

The present invention relates to a new and distinct cultivar of *Veronica*, given the name, 'TNVERA'. *Veronica* is in the family Plantaginaceae (formerly Scrophulariaceae). This new cultivar was found as a naturally occurring branch mutation at the nursery in Canby, Oreg. of *Veronica* hybrid 'Giles Van Hees', an unpatented plant. Compared to the mother plant, *Veronica* hybrid 'Giles Van Hees', the new cultivar has a larger plant size with larger inflorescences, darker pink flowers, and greater vigor. Compared to *Veronica spicata* 'Rotfuchs' RED FOX, an unpatented plant, the new cultivar is shorter with larger flowers. Compared to the other pink flowering *Veronica* on the market, the new cultivar has a more compact habit, darker flowers, and is more free-flowering.

The new cultivar exhibits the following characteristics:

1. warm pink flowers in free flowering spikes, with some rebloom in late summer,
2. a compact, slow spreading, low mounding habit,
3. excellent dense branching with flower spikes at end of every branch,
4. medium green leaves,
5. excellent vigor, and
6. good garden performance.

The new variety has been reproduced only by asexual propagation (stem cuttings and micropropagation). Each of the progeny exhibits identical characteristics to the original plant. Asexual propagation by division and micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of the flowers of the new cultivar.

FIG. 2 shows one-year-old *Veronica* 'TNVERA' growing in the trial field in May in Canby, Oreg.

DETAILED PLANT DESCRIPTION

The following is a detailed description of the new *Veronica* cultivar based on observations of one and a half-year-old specimens grown outside in the ground in early September in trial beds in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The Royal Horticultural Society Colour Chart, $5^{th}$ edition.

Plant:

*Form.*—Mat.
*Type.*—Evergreen, mat forming subshrub/perennial/small scale groundcover.
*Cold hardiness.*—USDA Zone 4-8.
*Size.*—Grows to 37 cm wide and 14 cm tall to the top of the foliage, 27 cm tall to the top of the flowers.
*Vigor.*—Excellent.
*Branching.*—Extremely well branched with about 40 stems from the crown, older stems branching freely.
*Stem.*—Grows to 14 mm long, pubescent, internodes range from 0.5 cm to 2 cm long, young stems Yellow Green 147C; older woody stems grow to 6 mm wide, Brown 200A.
*Roots.*—Fibrous, freely branching, plants root easily from stem tip cuttings in about 10 to 14 days.

Leaf:

*Type.*—Simple.
*Arrangement.*—Opposite.
*Average number of leaves per stem.*—About 20.
*Blade size.*—Grow to 35 mm long and 11 mm wide.

*Petiole description.*—11 mm long and 1 mm wide, pubescent, Yellow Green 147B.
*Shape.*—Lanceolate.
*Venation.*—Pinnate.
*Margins.*—Serrate.
*Apex.*—Acute.
*Base.*—Attenuate.
*Surface texture.*—Pubescent of both sides.
*Leaf color.*—Top side Green 137A with main vein 147B, bottom side Green 137B with main vein 147B.

Inflorescence:
*Type.*—Terminal raceme.
*Number of flowers.*—About 70 per raceme.
*Size of inflorescence.*—Spreads 2.5 cm wide and 15 cm long.
*Peduncle.*—15 mm to 20 mm long and 2 mm wide, pubescent, Yellow Green 147B.
*Pedicel.*—1 mm long and 1 mm wide, pubescent, Yellow Green 147B.
*Bloom period.*—Middle of May to end of June with some rebloom in August in Canby, Oreg.

Flower bud:
*Size.*—6 mm long and 2 mm wide at the widest point prior to opening.
*Description.*—Convolute, narrowly oblong, apex obtuse.
*Surface texture.*—Glabrous.
*Color.*—Red Purple 64A.

Flower:
*Type.*—Regular
*Shape.*—Rotate. .
*Corolla description.*—10 mm wide and 10 mm deep; both sides glabrous, tube 3 mm long and 1.5 to 2.5 mm wide, Red Purple 69A inside and out, 4 lobes, Red Purple 68B inside and 70B outside, upper lobe broadly obovate, 4 mm long and 5 mm wide, tip obtuse, margin erose, side and bottom lobes 6 mm long and 3 mm wide, obovate, tip obtuse, margin entire.
*Calyx description.*—Campanulate, 3 mm wide and 3 mm deep, 4-lobed, lobes ovate, tips acute, margins entire, Green 137A and pubescent on both sides.
*Pistil description.*—1, 8.5 mm long, ovary round, 1 mm long and 1 mm wide, Yellow Green 144A, style 7 mm long, Purple Violet N81A, stigma Violet 83A.
*Stamen description.*—2, filaments 9 mm long and Red Purple 73D, anthers 1.5 mm long and Purple Violet N81A, pollen none.
*Fragrance.*—None.
*Lastingness.*—A raceme blooms for about 2 weeks on the plant.

Fruit: An ovoid capsule 2.5 mm long and 2 mm wide, glabrous, Brown 200A.

Seed: None to date.

Pests and diseases: Disease and pest resistance is beyond what is typical for *Veronica* species.

I claim:

1. A new and distinct form of *Veronica* plant substantially as shown and described.

* * * * *

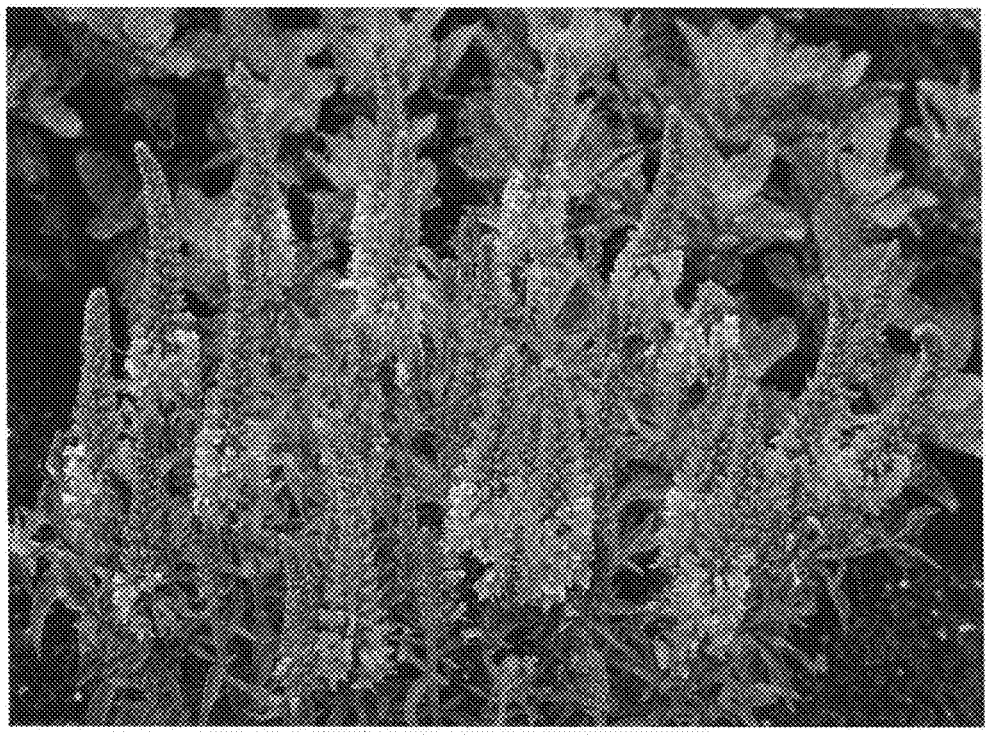

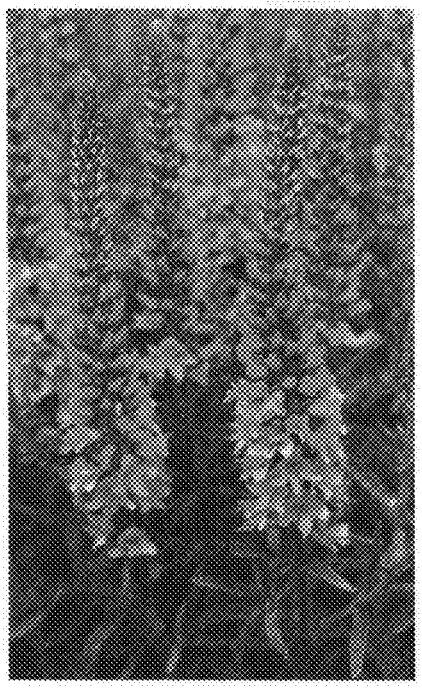
FIG. 1 on left
FIG. 2 below